(12) United States Patent
Miller

(10) Patent No.: US 10,111,620 B2
(45) Date of Patent: Oct. 30, 2018

(54) ENHANCED MOTION TRACKING USING TRANSPORTABLE INERTIAL SENSORS TO DETERMINE THAT A FRAME OF REFERENCE IS ESTABLISHED

(71) Applicant: MICROSOFT TECHNOLOGY LICENSING, LLC, Redmond, WA (US)

(72) Inventor: Quentin S. Miller, Sammamish, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 604 days.

(21) Appl. No.: 14/634,476

(22) Filed: Feb. 27, 2015

(65) Prior Publication Data

US 2016/0249856 A1 Sep. 1, 2016

(51) Int. Cl.
*A61B 5/00* (2006.01)
*G06F 3/0346* (2013.01)
*G01C 21/16* (2006.01)
*G06F 1/16* (2006.01)
*H04M 1/725* (2006.01)

(52) U.S. Cl.
CPC .......... *A61B 5/6803* (2013.01); *A61B 5/6887* (2013.01); *G01C 21/16* (2013.01); *G06F 1/163* (2013.01); *G06F 3/0346* (2013.01); *H04M 1/72569* (2013.01)

(58) Field of Classification Search
CPC ... A61B 5/6803; A61B 5/6887; G06F 3/0346; H04M 1/72569; G01C 21/16
See application file for complete search history.

(56) References Cited

U.S. PATENT DOCUMENTS

| | | |
|---|---|---|
| 5,645,077 A | 7/1997 | Foxlin |
| 6,050,822 A | 4/2000 | Faughn |
| 6,176,837 B1 | 1/2001 | Foxlin |
| 6,474,159 B1 | 11/2002 | Foxlin et al. |
| 6,633,267 B2 | 10/2003 | Numa |
| 6,757,068 B2 | 6/2004 | Foxlin |
| 7,312,766 B1 | 12/2007 | Edwards |
| 7,640,106 B1 | 12/2009 | Stokar et al. |

(Continued)

OTHER PUBLICATIONS

Uber Expansion: 2015 Uber Data & Stats (2015), pp. 1-4. Retrieved from World Wide Web at https://uberexpansion.com/2015-uber-data-stats/.*

(Continued)

*Primary Examiner* — Michael Jung
(74) *Attorney, Agent, or Firm* — Jacob P. Rohwer; Scott Y. Shigeta; Newport IP, LLC

(57) ABSTRACT

Technologies are described herein for providing enhanced motion tracking using a transportable inertial sensor. Configurations disclosed herein utilize a first inertial sensor mounted to a device to determine a frame of reference, and a second inertial sensor mounted to an object to determine movement of the object within the frame of reference. Configurations disclosed herein determine if the frame of reference is established. If it is determined that the frame of reference is established, the first inertial sensor and the second inertial sensor are used to detect movement of the object within the frame of reference.

18 Claims, 7 Drawing Sheets

(56) References Cited

U.S. PATENT DOCUMENTS

| | | | |
|---|---|---|---|
| 7,672,781 | B2 | 3/2010 | Churchill et al. |
| 7,717,841 | B2 | 5/2010 | Brendley et al. |
| 8,209,140 | B2 | 6/2012 | Bailey |
| 8,704,882 | B2 | 4/2014 | Turner |
| 8,767,306 | B1 | 7/2014 | Miao et al. |
| 2002/0194914 | A1 | 12/2002 | Foxlin et al. |
| 2004/0149036 | A1 | 8/2004 | Foxlin et al. |
| 2006/0284792 | A1 | 12/2006 | Foxlin |
| 2007/0132714 | A1 | 6/2007 | Nilsson |
| 2009/0189974 | A1 | 7/2009 | Deering |
| 2010/0216509 | A1 | 8/2010 | Riemer et al. |
| 2010/0321277 | A1 | 12/2010 | Spruck et al. |
| 2011/0260921 | A1 | 10/2011 | Harrat |
| 2012/0323515 | A1 | 12/2012 | Liu et al. |
| 2013/0124006 | A1 | 5/2013 | Anantha |
| 2013/0132246 | A1* | 5/2013 | Amin .................... G06Q 40/10 705/34 |
| 2013/0246301 | A1* | 9/2013 | Radhakrishnan .. G06Q 30/0282 705/347 |
| 2013/0265440 | A1 | 10/2013 | Mizuta |
| 2013/0336629 | A1 | 12/2013 | Mulholland et al. |
| 2014/0085183 | A1 | 3/2014 | Na |
| 2014/0098008 | A1 | 4/2014 | Hatton |
| 2014/0129135 | A1* | 5/2014 | Holden .................. G01C 21/30 701/420 |
| 2014/0129951 | A1* | 5/2014 | Amin .................... G06Q 50/30 715/738 |
| 2014/0139486 | A1 | 5/2014 | Mistry et al. |
| 2014/0364212 | A1 | 12/2014 | Osman et al. |
| 2015/0009187 | A1 | 1/2015 | Mercea et al. |
| 2015/0099461 | A1* | 4/2015 | Holden ............... G01C 21/367 455/39 |
| 2015/0143297 | A1* | 5/2015 | Wheeler .............. G06F 3/0485 715/830 |
| 2015/0161564 | A1* | 6/2015 | Sweeney ........ G06Q 10/063114 705/338 |
| 2015/0271290 | A1* | 9/2015 | Tao .................... H04L 41/5051 709/217 |
| 2016/0187974 | A1* | 6/2016 | Mallinson ............... G06F 3/014 463/32 |
| 2017/0038213 | A1 | 2/2017 | Han |
| 2017/0059886 | A1 | 3/2017 | Fayolle |

OTHER PUBLICATIONS

Uber Driver Data Report—Business Insider, Jan. 22, 2015, pp. 1-3. Retrived from Wordl Wide Web at http://www.businessinsider.com/uber-driver-data-report-2015-1.*

International Preliminary Report on Patentability Issued in PCT Application No. PCT/US2016/017045, dated Apr. 11, 2017, 12 Pages.

PCT Search Report and Written Opinion dated Apr. 28, 2016 for PCT Application No. PCT/US16/17045, 13 pages.

PCT Search Report and Written Opinion Issued in PCT Application No. PCT/US2016/017046, dated May 3, 2016, 13 Pages.

Almazan, et al., "Full Auto-Calibration of a Smartphone on Board a Vehicle using IMU and GPS Embedded Sensors", In IEEE Intelligent Vehicles Symposium, Jun. 23, 2013, pp. 1374-1380.

"Auto-alignment Platform", Published on: May 29, 2009, Available at; http://www.rpaelectronics.com/Visual-Simulation/auto-alignment-platform.html, 1 page.

Foxlin, et al., "FlightTracker: A Novel Optical/Inertial Tracker for Cockpit Enhanced Vision", In IEEE/ACM International Symposium on Mixed and Augmented Reality, Nov. 2, 2004, 10 pages.

Foxlin, et al., "Improved Registration for Vehicular AR Using Auto-Harmonization", In IEEE International Symposium on Mixed and Augmented Reality, Sep. 10, 2014, pp. 105-112.

"Inertial Measurement Unit (IMU)", Published on: Feb. 1, 2003, Available at: http://www.ssl.umd.edu/projects/RangerNBV/thesis/2-4-1.htm, 3 pages.

"Position Sensors", Published on: Jan. 7, 2012, Available at: http://developer.android.com/guide/topics/sensors/sensors_position.html, 6 pages.

"Wireless IMU", Retrieved on: Nov. 13, 2014, Available at: https://play.google.com/store/apps/details?id=org.zwiener.wimu&hl=en, 2 pages.

"Second Written Opinion Issued in PCT Application No. PCT/US2016/017046", dated Jan. 26, 2017, 11 Pages.

"Second Written Opinion Issued in PCT Application No. PCT/US2016/017045", dated Jan. 16, 2017, 11 Pages.

U.S. Appl. No. 14/634,579—Non Final Office Action, dated Aug. 11, 2017, 45 pages.

"Final Office Action Issued in U.S. Appl. No. 14/634,579", dated Apr. 26, 2018, 69 Pages.

* cited by examiner

ENHANCED MOTION TRACKING USING TRANSPORTABLE INERTIAL SENSORS TO DETERMINE THAT A FRAME OF REFERENCE IS ESTABLISHED

BACKGROUND

Inertial sensors are used in a wide range of applications for tracking the movement of objects, such as limbs, cameras, input devices, or head mounted displays (HMDs). In some examples, inertial tracking devices have been successfully applied to a wide range of applications including virtual environment (VE) training, virtual prototyping, interactive visualization and design, virtual reality (VR) gaming, and vehicle simulation. Despite the level of accuracy provided by some inertial sensors, some existing technologies cannot be used in certain applications. For example, when an inertial sensor is used to track the movement of an object in a moving vehicle, the signal produced by the inertial sensor cannot be relied upon because the inertial sensor cannot determine if inertial forces are caused by the vehicle or the object.

To overcome some of the shortcomings of existing technologies, some devices configured with an inertial sensor are enhanced with visual tracking sensors. For example, in addition to using an inertial sensor, some devices have one or more cameras to track the movement of an object. However, solutions using visual tracking sensors are not as efficient as solutions using inertial sensors when it comes to computing resources and power consumption.

It is with respect to these and other considerations that the disclosure made herein is presented.

SUMMARY

Technologies are described herein for providing enhanced motion tracking using a transportable inertial sensor. Configurations disclosed herein utilize an inertial sensor mounted to a device to determine a frame of reference, and another inertial sensor mounted to an object to detect, monitor and/or analyze the movement of the object within the frame of reference. Configurations disclosed herein selectively utilize the inertial sensor mounted to the device depending on one or more factors. In some configurations, techniques described herein determine if the frame of reference is established. If it is determined that the frame of reference is established, the inertial sensor mounted to the device and the inertial sensor mounted to the object are used to detect, monitor and/or analyze the movement of the object within the frame of reference. If the frame of reference is not established, configurations disclosed herein may use the inertial sensor mounted to the object to detect, monitor and/or analyze movement of the object.

It should be appreciated that the above-described subject matter may be implemented as a computer-controlled apparatus, a computer process, a computing system, or as an article of manufacture such as a computer-readable storage medium. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

Figure 1:
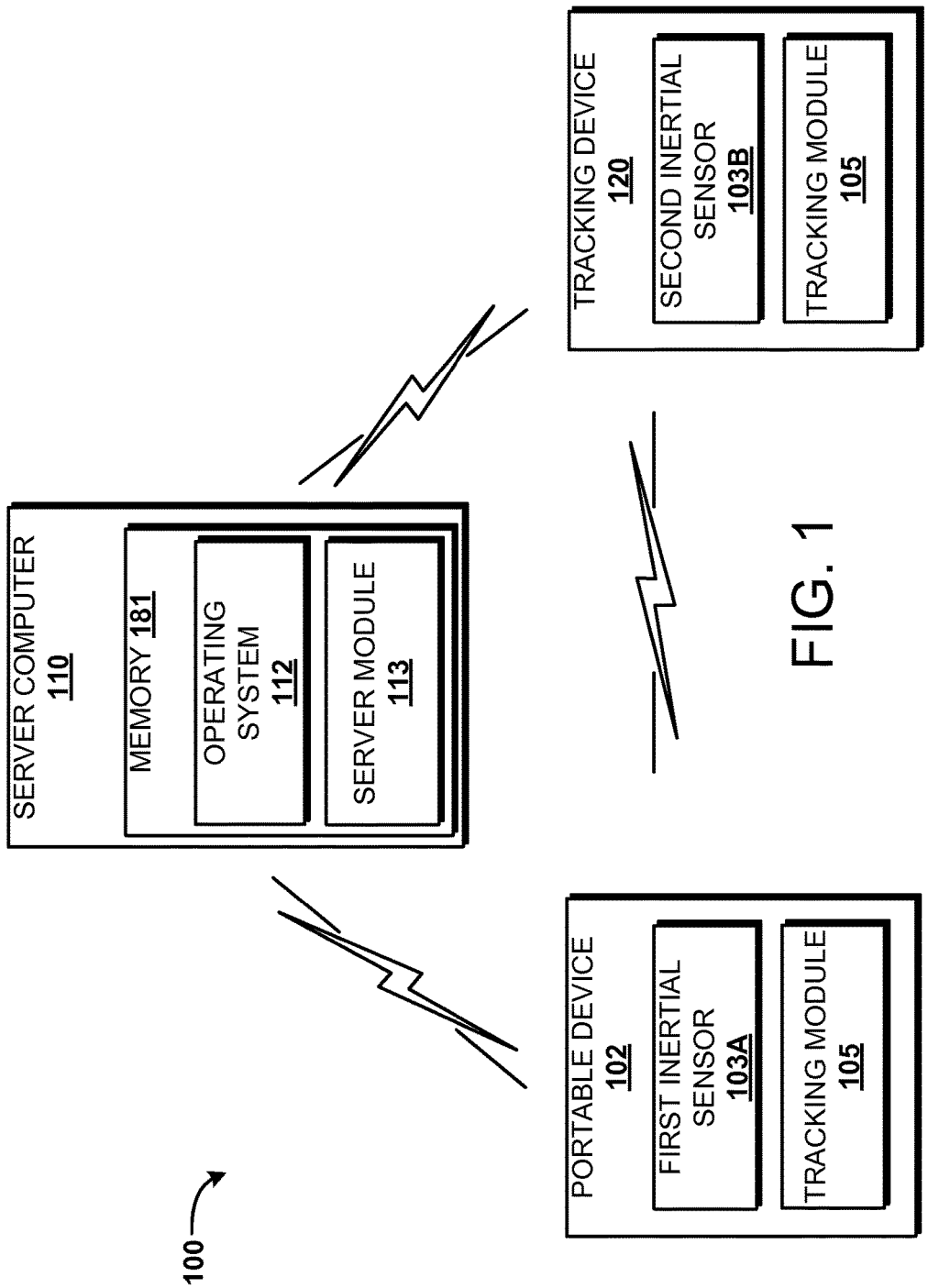
FIG. 1 is a block diagram showing several example components of a system for providing enhanced motion tracking using a transportable inertial sensor.

The following detailed description is directed to concepts and technologies for providing enhanced motion tracking using a transportable inertial sensor. Configurations disclosed herein utilize an inertial sensor mounted to a portable device to determine a frame of reference, and an inertial sensor mounted to an object to detect, monitor and/or analyze the movement of the object within the frame of reference. Configurations disclosed herein selectively utilize the inertial sensor mounted to the portable device depending on one or more factors. In some configurations, techniques described herein determine if the frame of reference is established. If it is determined that the frame of reference is established, the inertial sensor mounted to the portable device and the inertial sensor mounted to the object are used to detect, monitor and/or analyze the movement of the object within the frame of reference. If it is determined that the frame of reference is not established, configurations disclosed herein may only use the inertial sensor mounted to the object to detect, monitor and/or analyze movement of the object.

By use of the techniques and technologies described herein, a transportable inertial sensor may be selectively utilized with another inertial sensor to detect, monitor and/or analyze the movement of an object relative to a vehicle. In one illustrative example, a system may include a mobile phone configured with an inertial sensor. The mobile phone is in communication with a head-mounted display (HMD) configured with another inertial sensor. When a user wearing the HMD enters a vehicle, the user may secure the phone to the vehicle, e.g., place the phone on a surface within the vehicle or affix the phone to the vehicle.

The system utilizes the inertial sensor of the phone to determine a frame of reference. Utilizing one or more factors based on an input and/or contextual data, the system determines that the frame of reference is established. Once the system determines that the frame of reference is established, the system utilizes a signal from the inertial sensor of the phone and a signal of the inertial sensor of the HMD to track the movement of the HMD relative to the frame of reference. Since the phone is secured to the vehicle, the frame of reference is associated with the vehicle and the system may distinguish acceleration that is applied to the HMD from acceleration that is caused by movement of the vehicle.

The use of a portable device, such as a phone, tablet, phablet or computer, enables the user to transport a set of sensors from one vehicle to another vehicle with little or no user interaction to conform the sensors to a new vehicle. The transportability and/or portability of the sensors is attributed, at least in part, to techniques that selectively utilize the inertial sensor of the portable device.

As will be described in more detail herein, the system may utilize one or more factors to determine if a frame of reference is established. Among many examples described herein, the system may determine that the frame of reference is established if the portable device is sufficiently affixed to the vehicle. In some configurations, sensors in the portable device and/or the vehicle can be used to determine if the portable device is sufficiently affixed to the vehicle. In other configurations, an input, which may include a user input, a signal from one or more inertial sensors and/or contextual data may be used to determine if the frame of reference is established.

Once it is determined that the frame of reference is established, the system may utilize the inertial sensor of the portable device in conjunction with the inertial sensor of a tracking device, such as a HMD, to detect, monitor and/or analyze the movement of an object relative to the frame of reference. With reference to the above-described example, when the user desires to move to another vehicle, the phone and the HMD may be easily transported with the user. The system and techniques disclosed herein do not rely on resource-consuming cameras or other sensors affixed to the vehicle.

While the subject matter described herein is primarily presented in the general context of techniques for providing enhanced motion tracking using a transportable inertial sensor, it can be appreciated that the techniques described herein may apply to any type of sensor and/or any type of device embodying the sensors. As will be described in more detail herein, it can be appreciated that implementations of the techniques and technologies described herein may include the use of solid state circuits, digital logic circuits, computer component, and/or software executing on one or more devices. Signals described herein may include analog and/or digital signals for communicating a changed state, movement and/or any data associated with motion detection.

While the subject matter described herein is presented in the general context of program modules that execute in conjunction with the execution of an operating system and application programs on a computer system, those skilled in the art will recognize that other implementations may be performed in combination with other types of program modules. Generally, program modules include routines, programs, components, data structures, and other types of structures that perform particular tasks or implement particular abstract data types. Moreover, those skilled in the art will appreciate that the subject matter described herein may be practiced with other computer system configurations, including hand-held devices, multiprocessor systems, microprocessor-based or programmable consumer electronics, minicomputers, mainframe computers, and the like.

In the following detailed description, references are made to the accompanying drawings that form a part hereof, and in which are shown by way of illustration specific configurations or examples. Referring now to the drawings, in which like numerals represent like elements throughout the several figures, aspects of a computing system, computer-readable storage medium, and computer-implemented methodologies for providing enhanced motion tracking using a transportable inertial sensor. As will be described in more detail below with respect to FIGS. 5-7, there are a number of applications and services that can embody the functionality and techniques described herein.

FIG. 1 is a system diagram showing aspects of one illustrative mechanism disclosed herein for providing enhanced motion tracking using a transportable inertial sensor. As shown in FIG. 1, the system 100 includes a first inertial sensor 103A mounted to a portable device 102 and a second inertial sensor 103B mounted to a tracking device 120. In some configurations, the system 100 utilizes the first inertial sensor 103A to determine a frame of reference. The system 100 also utilizes the second inertial sensor 103B to track movement of the tracking device 120 relative to the frame of reference. For illustrative purposes, the first inertial sensor 103A and the second inertial sensor 103B are individually and generically referred to herein as a "sensor 103" or "sensors 103." Optionally, a server module 113 and an operation system 112 of a server computer 110 may be used to implement one or more aspects of the techniques described herein.

Generally described, the tracking device 120 may be worn by a user in a manner such that the second inertial sensor 103B is mounted to an object, such as a user's head. The second inertial sensor 103B generates a signal indicating movement of the object. In addition, the first inertial sensor 103A is mounted to the portable device 102. When the portable device 102 is place on a surface of a vehicle or any other movable platform carrying the user and the tracking device 120, the system 100 utilizes the signal generated by the first inertial sensor 103A to determine a frame of reference. The system 100 processes the signals from the first inertial sensor 103A and the second inertial sensor 103B to track the movement of the object within the frame of reference. Since the portable device 102 is affixed or secured to the vehicle such that the frame of reference follows the movement of the vehicle, the system 100 can track, detect and/or monitor movement of the object relative to the vehicle.

While in operation, the system determines a difference, e.g., some measured delta, between the signal of the first inertial sensor 103A and the signal of the second inertial sensor 103B to track, detect and/or monitor movement of the object relative to the frame of reference. When the difference between the signal of the first inertial sensor 103A and the signal of the second inertial sensor 103B do not meet a threshold, the system 100 determines that the tracking device 120 is not moving within the frame of reference. If both sensors 103 generate similar signals, e.g., with the delta between the two signals being below a threshold, the system 100 can determine that the tracking device 120 is not moving within the frame of reference. In such a scenario, by use of the techniques presented herein, the system 100 may still determine that the tracking device 120 is not moving within the frame of reference even if the vehicle carrying the user and the tracking device 120 is accelerating, e.g., braking, turning, or increasing speed. However, when the difference between the signal of the first inertial sensor 103A and the signal of the second inertial sensor 103B meet the threshold, the system 100 can determine that the tracking device 120 is moving within the frame of reference. Such a scenario may indicate that an object attached to the tracking device 120 is moving within the vehicle.

The use of a portable device 102 configured to selectively utilize a first inertial sensor 103A with a second inertial sensor 103B allows the system 100 to be used in a moving vehicle with little or no user interaction to conform the system 100 to the vehicle or moving platform. The transportability and/or portability of the sensors 103 between vehicles is attributed, at least in part, to techniques that selectively utilize the first inertial sensor 103A based on the establishment of a frame of reference. As will be described in more detail herein, the system 100 may utilize one or more factors to determine if a frame of reference is established.

Among many examples described herein, the system 100 may determine that the frame of reference is established if the portable device 102 is sufficiently affixed to a vehicle or moving platform. In some configurations, one or more sensors or contact pads of the portable device 102 and/or a vehicle may indicate if the portable device 102 is affixed to the vehicle. As will be described below, other forms of input data and/or contextual data may be used to determine if the frame of reference is established.

Once it is determined that the frame of reference is established, the system 100 may utilize the inertial sensor of the portable device 102 in conjunction with the inertial sensor of the tracking device 120 to detect, monitor and/or analyze the movement of an object mounted to the tracking device 120 relative to the frame of reference. In some configurations, when the system 100 determines that the frame of reference is no longer established, e.g., when the portable device 120 becomes detached from the vehicle, the system 100 no longer utilizes the inertial sensor of the portable device 102. Using the techniques and technologies disclosed herein, the portable device 102 and the tracking device 120 may be easily transported when the user desires to move to another vehicle.

Techniques for determining if the frame of reference is established may be based on a number of factors using a number of different inputs from different devices. For instance, the system 100 may utilize an input from one or more users. In such an example, by the utilization of a user interface ("UI") or any other gesture recognition technology, an input may indicate that the frame of reference is established or that the portable device 120 is in a suitable position for establishing the frame of reference.

In another example, the system 100 may receive contextual data from the vehicle or another device indicating that the frame of reference is established or that the portable device 120 is in a suitable position for establishing the frame of reference. Contextual data may be received by any type of device, such as a proximity sensor, camera or a global positioning unit. The contextual data may include any type of information, such as user activity, user preferences, one or more thresholds, the status of a device, the status of a vehicle and/or any other information that can be used to determine if a frame of reference is established. Such contextual data may be used to interpret one or more factors, which may be used to determine if the frame of reference is established or that the portable device 120 is in a suitable position for establishing the frame of reference.

In another example, the system 100 may analyze the signals generated from one or more of the sensors 103 to determine if a frame of reference has been established. In one illustrative example, the system 100 may monitor a signal generated by the inertial sensor 103A of the portable device 102, if the signal indicates that the movement of the portable device 102 is within a threshold for a pre-determined period of time, the system 100 may determine that a frame of reference is established.

In yet another example, the system 100 may monitor the signal generated by the inertial sensor 103A of the portable device 102 and the signal generated by the inertial sensor 103B of the tracking device 120. In such an example, when the difference between the two signals indicates a particular pattern and/or level, the system 100 may determine that the portable device 102 and the tracking device 120 are in a vehicle together and that a frame of reference may be established. For instance, if both sensors identify identical patterns of acceleration, e.g., a jet taking off or a car making a turn, the system 100 may determine that the frame of reference may be established.

In some configurations, the system 100 may interpret a pattern and/or characteristic of the signal from one or more inertial sensors 103 and determine that a frame of reference may be established based on the pattern and/or characteristic. Various patterns or one or more characteristics of the signal may indicate that a device has been placed on a surface, positioned in a mount or otherwise stabilized for establishing a frame of reference.

Techniques involving signals generated from one or more of the internal sensors 103 may be combined with other techniques involving other forms of input or contextual data to determine if the frame of reference is established or that the portable device 120 is in a suitable position for establishing the frame of reference. For example, techniques involving contextual data and a user input may be used in combination with a technique involving a comparison of a threshold with a sensor signal to determine that a frame of reference has been established. Any data providing context relating to the user, the portable device 102, the tracking device 120 may be used to determine if the frame of reference is established or that the portable device 120 is in a suitable position for establishing the frame of reference.

In some configurations, the portable device 102, the tracking device 120 and the server computer 110 may operate as stand-alone devices. In such configurations, the portable device 102, the tracking device 120 and the server computer 110 may be configured individually to perform the techniques described herein. In other configurations, the portable device 102, the tracking device 120 and the server computer 110 may be configured to operate in concert to perform the techniques described herein. In addition, the portable device 102, the tracking device 120 and the server computer 110 may be interconnected through one or more communication mechanisms, which may include wired or wireless connections. In addition, the communication of the devices and computers of FIG. 1 may include the use of local and/or wide area networks or other forms of communication, which may involve BLUETOOTH, Wi-Fi or other types of communication mechanisms.

The portable device 102 may be any type of computing device, such as a mobile phone, a tablet, a phablet, a laptop computer, a combination of computers or a desktop computer. The portable device 102 may be a customized device, referred to herein as a "puck," having one or more sensors, at least one processor and communication modules.

In some configurations, the portable device 102 may include a display interface for displaying data. The portable device 102 may also include an input device for receiving input from the user. The display interface may be a touch-sensitive display screen that is operable to display images and/or video data, and also operable to receive input from the user, input that may involve a touch signal that indicates an input gesture. One or more sensors, such as the first sensor 103A, may be used to generate data and/or a signal indicating a movement and/or a user input gesture. As described herein and shown in FIG. 5 and FIG. 7, the portable device 102 may also include memory for storing programs and data.

The tracking device 120 may be any type of device. In some examples, the tracking device 120 may be a wearable device such as a watch, HMD or any other device used to track and/or monitor the movement of an object. The tracking device 120 may be configured with solid state components and/or computer components that implement the techniques described herein. The tracking device 120 may optionally include a display interface for displaying data and/or an input device for receiving input from the user. The display interface may be a touch-sensitive display screen that is operable to display images and/or video data, and also operable to receive input from the user, input that may involve a touch signal or a video signal captured by a camera that indicates an input gesture. For instance, a camera mounted to an HMD may capture a user's hand movements as an input. One or more sensors, such as the second sensor 103B, may be used to generate data and/or a signal indicating a movement and/or a user input gesture.

The sensors 103 may include an individual device or combination of devices for measuring the velocity and/or position. For example, the sensors 103 may include an accelerometer capable of measuring acceleration in one, two, or three orthogonal axes. The sensors 103 can include Micro-Electro-Mechanical Sensors (MEMS) or other configurations capable of measuring acceleration in one or more axes. An output signal of the sensor 103 may be digital or analog and include a range of values indicative of movement, sensitivity and/or other values related to acceleration.

The server computer 110 may be any type of computing device, such as a personal computer, a server or a number of computing devices configured to perform aspects of the techniques described herein. The server computer 110 may include memory 181 for storing an operating system 112 and a server module 113 that is configured to aspects of the techniques and technologies disclosed herein. As will be described below, the server computer 110 may include other components for implementing aspects of the techniques and technologies disclosed herein. For instance, contextual data used by the system 100 may be interpreted from user activity or activity of other services and platforms, such as a social network. Contextual data generated by such activity may be generated or received by the computer server 110 or other computers or services, such as those described below and shown in FIG. 6.

Figure 2:
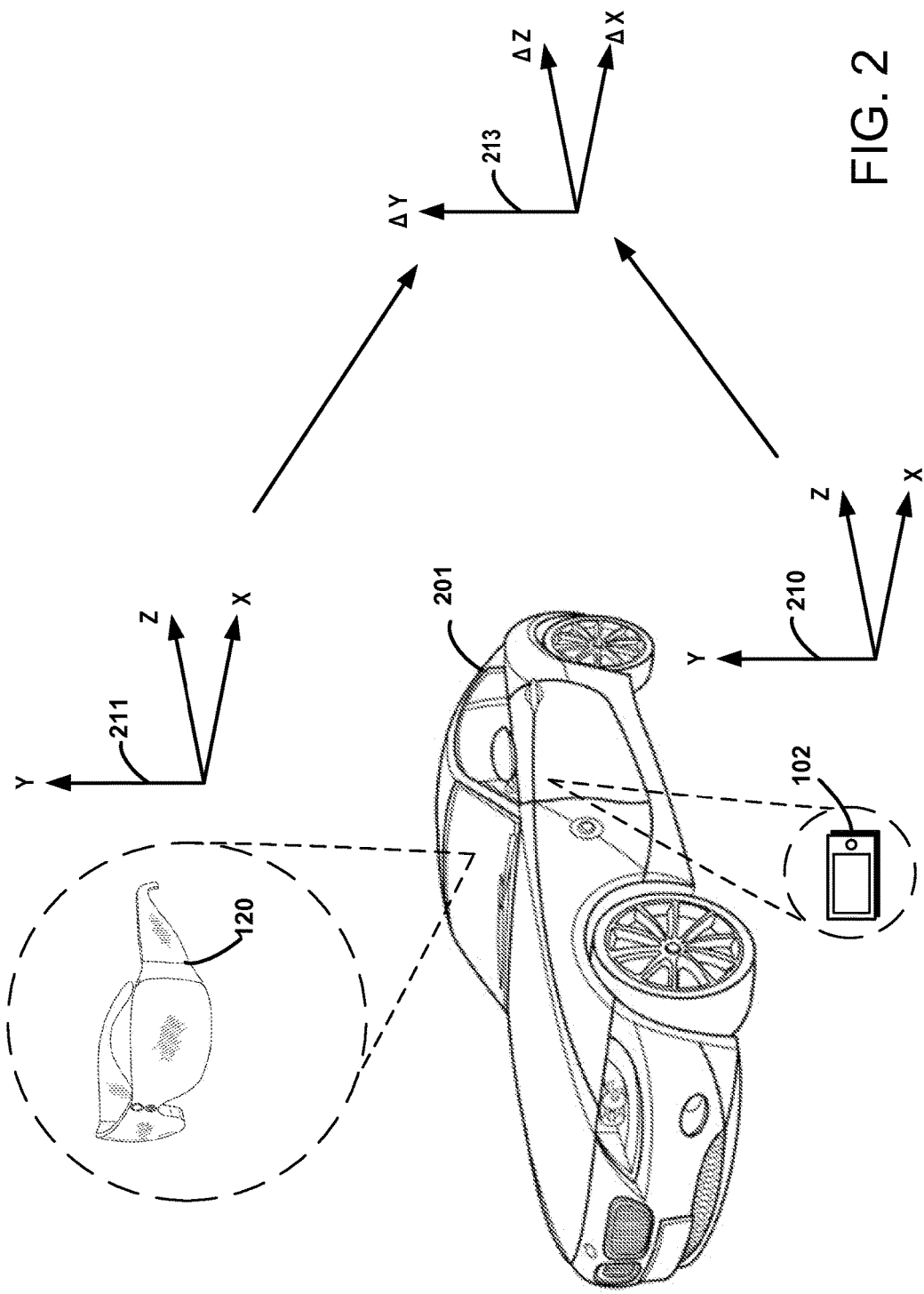
FIG. 2 is a pictorial diagram that illustrates representations of a portable device and a tracking device positioned in a car.
Figure 3:
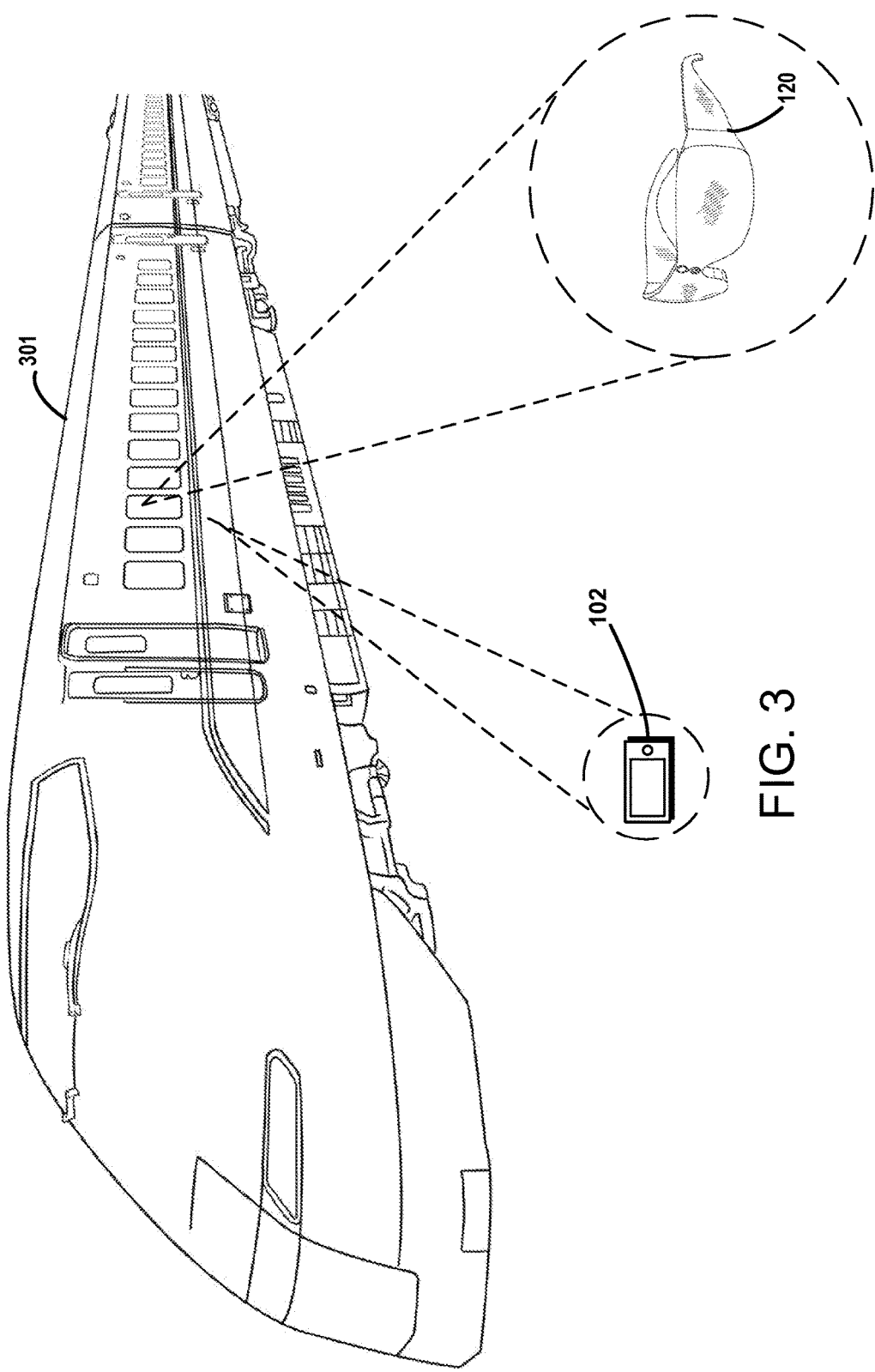
FIG. 3 is a pictorial diagram that illustrates representations of a portable device and a tracking device positioned in a train.

Turning now to FIGS. 2-3, an illustrative example shows how a configuration of the system 100 may be utilized. In this example, to show various aspects, such as the portability and utility of the system 100, it is given that a user is wearing a tracking device 120, such as an HMD, and carrying a portable device 102, such as a mobile phone. As described above, the portable device 102 has a first sensor 301A and the tracking device 120 has a second sensor 103B. In this example, the techniques described herein allow the user to operate the system 100 in multiple vehicles with little or no user interaction to coordinate the tracking device 120 and the portable device 102.

FIG. 2 illustrates representations of the portable device 102 and the tracking device 120 positioned in a car 201. In the current example, when the user enters the car 201, it is given that the user places the portable device 102 in a position that allows the portable device 102 to be sufficiently affixed to the car 201 such that the motion of the portable device 102 follows the motion of the car 201. For instance, the portable device 102 may be placed on a surface, e.g., a dashboard or center console, or mounted to the car 201 using a brace or a custom rack. Using techniques described herein, the system 100 determines that a frame of reference has been established.

Upon determining that the frame of reference has been established, the system 100 then utilizes the sensors (301A and 103B), which are both positioned within the car 201. As shown in FIG. 2, the movement of the portable device 102 is represented by the first vector model 210. In addition, the movement of the tracking device 120 is represented by the second vector model 211. The system 100 analyzes and processes the relative difference between the signals of the two sensors (301A and 103B) to determine the movement of the tracking device 120 relative to the portable device 102. Using the relative difference between the signals, the movement of the tracking device 120 relative to the portable device 102 detected, which is represented by the third vector model 213. Specific to the illustrative example, the system 100 may determine the movement of the HMD relative to a frame of reference that follows the motion of the car 201.

Any technique or combination of techniques for processing two or more signals to identify a measured delta between the sensor signals may be used to implement the techniques described herein. The resulting output, modeled by the third vector model 213, may be used by the system 100 to determine the movement of the tracking device 120, e.g., the HMD, relative to the car 201, regardless of the acceleration that is generated by the car 201.

In the current example, by use of the techniques described herein, when the user exits the car 201 and moves the portable device 102, the system 100 determines that the frame of reference is no longer established. In some configurations, when the frame of reference is no longer established, the system 100 may only utilize sensor of the tracking device 120. The system 100 may determine if the frame of reference is no longer established by the use of one or more factors described herein. For example, the system 100 may receive an input, a signal from one or more sensors and/or contextual data. An input or contextual data may be analyzed to determine one or more factors indicating that the frame of reference is no longer valid and/or that the portable device 102 is no longer attached to the car 201. As also described herein, any combination of signals generated by one or more sensors, a user input and/or contextual data may be used to determine if the frame of reference is no longer established.

Next, in FIG. 3, in continuing the current example, the user may move from the car 201 to a train 301. In doing so, the user may place the portable device 102 in a position that sufficiently affixes the portable device 102 to the train 301. By the use of one or more factors described herein, the system 100 determines if the frame of reference is established. After the frame of reference is established, the system 100 may utilize the portable device 102 and the tracking device 120 to track, monitor and/or analyze the movement of the tracking device 120 in a manner as described herein.

By the use of the techniques described herein, the system 100 can track, detect and/or monitor movement of an object relative to a vehicle. In addition, the techniques described herein may allow a user to transport components of the system 100 from one vehicle to another with little or no user interaction to conform the system 100 to a new vehicle or moving platform.

Figure 4:
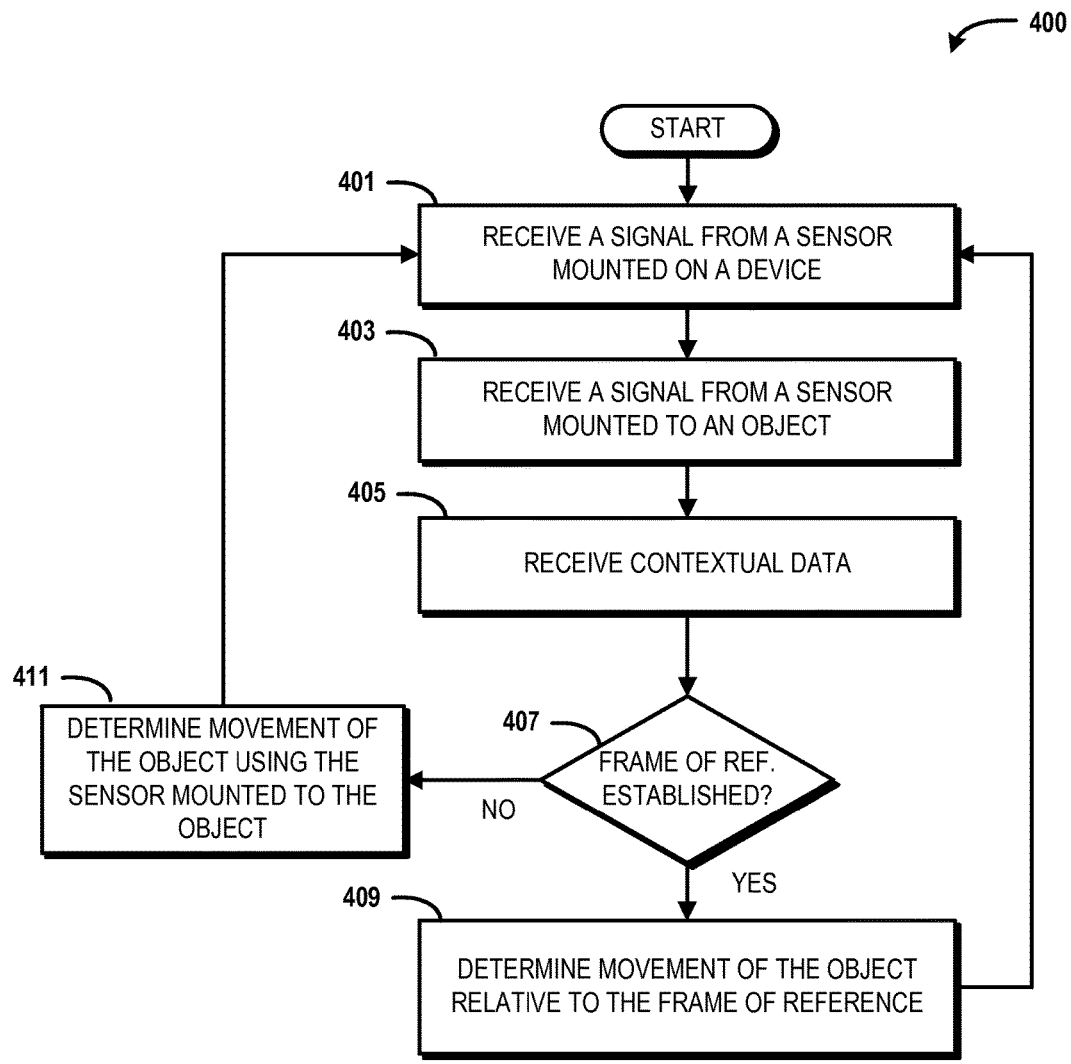
FIG. 4 is a flow diagram showing aspects of a routine disclosed herein for providing enhanced motion tracking using a transportable inertial sensor.

Turning now to FIG. 4, aspects of a routine 400 for providing enhanced motion tracking using a transportable inertial sensor are shown and described below. It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the appended claims.

It also should be understood that the illustrated methods can be ended at any time and need not be performed in its entirety. Some or all operations of the methods, and/or substantially equivalent operations, can be performed by execution of computer-readable instructions included on a computer-storage media, as defined below. The term "computer-readable instructions," and variants thereof, as used in the description and claims, is used expansively herein to include routines, applications, application modules, program modules, programs, components, data structures, algorithms, and the like. Computer-readable instructions can be implemented on various system configurations, including single-processor or multiprocessor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These operations, structural devices, acts, and modules may be implemented in software, in firmware, in special purpose digital logic, and any combination thereof.

As will be described in more detail below, in conjunction with FIGS. 5-7, the operations of the routine 400 are described herein as being implemented, at least in part, by an application and/or circuit, such as the tracking module 105. Although the following illustration refers to the tracking module 105, it can be appreciated that the operations of the routine 400 may be also implemented in many other ways. For example, the routine 400 may be implemented, at least in part, by the server module 113. In addition, one or more of the operations of the routine 400 may alternatively or additionally be implemented, at least in part, by the tracking module 105 of the portable device 102 and/or the tracking module 105 of the tracking device 120 working alone or in conjunction with other software modules, such as the one or more application servers 608 of FIG. 6. Any service, circuit or application suitable for providing contextual data indicating the position or state of any device may be used in operations described herein.

With reference to FIG. 4, the routine 400 begins at operation 401, where the tracking module 105 obtains a signal from at least one inertial sensor mounted to a device. In some configurations, a device, such as the portable device 102 described above, may be configured with one or more inertial sensors and circuitry for communicating and/or processing signals generated by the one or more inertial sensors. In some illustrative examples, the device may be in the form of a mobile phone, a tablet, a Wi-Fi hub, a computer or a customized device referred to as a "puck."

Next, at operation 403, the tracking module 105 obtains a signal from at least one inertial sensor mounted to an object. In some configurations, a tracking device 120 may be mounted to an object, such as a limb, camera, input device. As described above, one form of the tracking device 120 includes an HMD formed to mount to a user's head. In such an example, movement of the HMD and the mounted inertial sensors track the movement of the user's head.

Next, at operation 405, as an optional operation of routine 400, the tracking module 105 obtains contextual data. In some configurations, the contextual data 113 may be obtained from a single device or aggregated from a number of devices and/or resources. The contextual data may include data describing user activity, user preferences, location data and/or other information. Among other types of information, the contextual data may also describe the capabilities and/or a status of one or more devices.

In some configurations, the contextual data may be interpreted from user activity, e.g., a user's location based on another sensor, such as a GPS device, or activity on a social network or any other platform. The contextual data may be explicit, e.g., any signal or input entered directly by the user or implicit, e.g., interpreted from other types of activity. For example, one or more resources may interpret data from images, videos, text messages, emails, voice calls or any other form of communication to generate or obtain contextual data.

The contextual data may also come from a user profile or another data source indicating one or more user preferences. For instance, a user may indicate in a profile that they prefer to have a frame of reference established when their mobile phone is mounted to a vehicle in a certain way, e.g., a mount or rack. The contextual data may also indicate a number of other preferences, such as thresholds or user habits which can be used to determine if a frame of reference is established. The contextual data may also indicate the status of a device, such as a car, train or a vehicle. For instance, the contextual data may indicate if a car is running. These examples are provided for illustrative purposes only and are not to be construed as limiting. The contextual data may include any type of information from any resource. As described below with respect to operation 407, the contextual data may be combined with one or more signals from the sensors 103 or other forms of input to determine if a frame of reference has been established.

Next, at operation 407, the tracking module 105 determines if a frame of reference has been established. As described herein, techniques for determining if the frame of reference is established may be based on a number of factors using a number of inputs from one or more devices and/or resources. For instance, the tracking module 105 may utilize an input from one or more users. In such an example, by the utilization of a UI, an input or a gesture recognition technology, an input may indicate that the portable device 120 is in a suitable position for establishing a frame of reference.

In another example, the system 100 may utilize signals from one or more sensors 301. For instance, the tracking module 105 may receive a signal from the sensor of the portable device 102 and the pattern or at least one characteristic of the signal may indicate that the portable device 102 is in a position suitable for establishing a frame of reference. The signal may indicate a particular position, angle or a pattern of movement that indicates that portable device 102 is in a position suitable for establishing a frame of reference.

In addition, the tracking module 105 may utilize a signal from the sensor of the portable device 102 and the sensor of the tracking device 120 to determine if the portable device 102 is in a position suitable for establishing a frame of reference. For example, the system 100 may determine that the frame of reference is established if the signal from the sensor of the portable device 102 and the signal from the sensor of the tracking device 120 have a delta that is below a given threshold for a period of time. In another example, the system 100 may determine that the frame of reference is established if the signal from the sensor of the portable device 102 and/or the signal from the sensor of the tracking device 120 follow a particular pattern or characteristic. Patterns or characteristics of one or more sensor signals may indicate that both sensors are in the same vehicle. The use of signals from a single sensor or multiple sensors may also be combined with other received data, such as a user input, to determine if the frame of reference may be established.

Operation 407 may also involve the analysis of contextual data, which may be received in the form of a file or any other data structure. The contextual data may include location information, audio data, video data or any other information that provides context to a scenario or status related to the user and/or the system 100. The contextual data may also include data describing user activity, a user preference or one or more thresholds. The user activity may include data from any system or platform, such as a social network and/or a server working with the portable device 102 and the tracking device 120. In addition, operation 407 may utilize the contextual data alone or with other forms of input, such as the signals from one or more sensors and/or a user input.

At operation 407, if it is determined that the frame of reference is established, the routine 400 proceeds to operation 409 where the system 100 utilizes the inertial sensor of the portable device 102 in conjunction with the inertial sensor of the tracking device 120 to detect, monitor and/or analyze the movement of the object relative to the frame of reference. As described herein, and shown in FIG. 1 and FIG. 2, the system 100 analyzes and processes the relative difference between the signals of the two sensors (301A and 103B) to determine the movement of the tracking device 120 relative to the portable device 102. When the tracking device 120 is mounted to the object, the system 100 may determine the movement of the object relative to a frame of reference or any other object that moves with the frame of reference. In operation 409, any technique or combination of techniques for processing two or more signals to identify a measured delta between at least two sensor signals may be used to implement the techniques described herein.

At operation 407, if it is determined that the frame of reference is not established, the routine 400 proceeds to operation 409 where the system 100 may only utilize the inertial sensor 103B of the tracking device 120 to detect, monitor and/or analyze the movement of the object. While the frame of reference is not established, the routine 400 may cycle through operations 401-407 and 411 where the system 100 only utilizes one sensor, e.g., the inertial sensor 103B of the tracking device 120 to detect, monitor and/or analyze the movement of the object.

While the frame of reference is established, the routine 400 may cycle through operations 401 and 409 to continually monitor the signal of the sensors (301A and 103B) and/or the contextual data to detect, monitor and/or analyze the movement of the object within the frame of reference.

By providing a technique that enables the use of a single sensor or multiple sensors of multiple devices depending on one or more inputs and/or contextual data, the components of the system 100 may be easily transported with the user when the user desires to move to another vehicle.

In some configurations, the system 100 may provide an indication that the frame of reference is established. For example, when it is determined that the frame of reference is established, the tracking device 120 may generate a signal to provide notification to a user. In some configurations, the tracking device 120 may also provide a control allowing the user to accept or deny the use of the frame of reference. For instance, when the tracking device 120 issues a notification that the frame of reference is established, the user may provide an input indicating that they accept the use of the frame of reference. In response to receiving an input indicative of the acceptance, the inertial sensor 103A mounted to the portable device 102 is used to determine a frame of reference, and the tracking device 120 is used to track the movement of an object relative to the frame of reference. If the user denies the use of the reference sensor, the tracking device 120 is used to track the movement of an object.

The indication generated by the tracking device 120 may be any signal, sound, light and/or a mechanical actuation. For example, an element of a user interface may appear and/or a sound may be generated to alert a user. In other configurations, the tracking device 120 may initiate another form of communication or notice, e.g., a device may vibrate and/or cause a signal to activate another device.

Figure 5:
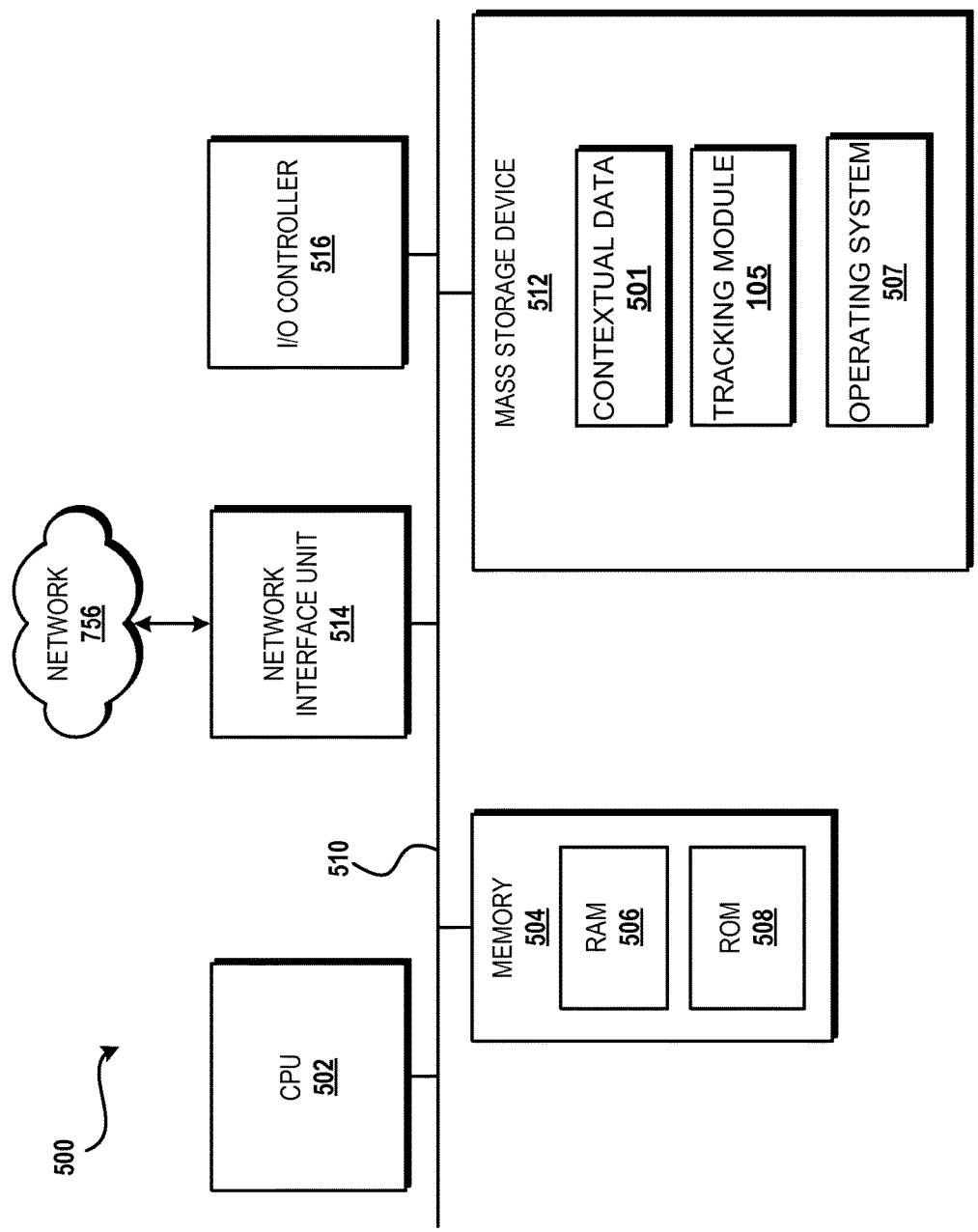
FIG. 5 is a computer architecture diagram illustrating an illustrative computer hardware and software architecture for a computing system capable of implementing aspects of the techniques and technologies presented herein.

FIG. 5 shows additional details of an example computer architecture 500 for a computer, such as the computing device 101 (FIG. 1), capable of executing the program components described above for providing enhanced motion tracking using a transportable inertial sensor. Thus, the computer architecture 500 illustrated in FIG. 5 illustrates an architecture for a server computer, mobile phone, a PDA, a smart phone, a desktop computer, a netbook computer, a tablet computer, and/or a laptop computer. The computer architecture 500 may be utilized to execute any aspects of the software components presented herein.

The computer architecture 500 illustrated in FIG. 5 includes a central processing unit 502 ("CPU"), a system memory 504, including a random access memory 506 ("RAM") and a read-only memory ("ROM") 508, and a system bus 510 that couples the memory 504 to the CPU 502. A basic input/output system containing the basic routines that help to transfer information between elements within the computer architecture 500, such as during startup, is stored in the ROM 508. The computer architecture 500 further includes a mass storage device 512 for storing an operating system 507, and one or more application programs including, but not limited to, a tracking module 105 and contextual data 501.

The mass storage device 512 is connected to the CPU 502 through a mass storage controller (not shown) connected to the bus 510. The mass storage device 512 and its associated computer-readable media provide non-volatile storage for the computer architecture 500. Although the description of computer-readable media contained herein refers to a mass storage device, such as a solid state drive, a hard disk or CD-ROM drive, it should be appreciated by those skilled in the art that computer-readable media can be any available computer storage media or communication media that can be accessed by the computer architecture 500.

Communication media includes computer readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

By way of example, and not limitation, computer storage media may include volatile and non-volatile, removable and non-removable media implemented in any method or technology for storage of information such as computer-readable instructions, data structures, program modules or other data. For example, computer media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer architecture 500. For purposes the claims, the phrase "computer storage medium," "computer-readable storage medium" and variations thereof, does not include waves, signals, and/or other transitory and/or intangible communication media, per se.

According to various configurations, the computer architecture 500 may operate in a networked environment using logical connections to remote computers through the network 756 and/or another network (not shown). The computer architecture 500 may connect to the network 756 through a network interface unit 514 connected to the bus 510. It should be appreciated that the network interface unit 514 also may be utilized to connect to other types of networks and remote computer systems. The computer architecture 500 also may include an input/output controller 516 for receiving and processing input from a number of other devices, including a keyboard, mouse, or electronic stylus (not shown in FIG. 5). Similarly, the input/output controller 516 may provide output to a display screen, a printer, or other type of output device (also not shown in FIG. 5).

It should be appreciated that the software components described herein may, when loaded into the CPU 502 and executed, transform the CPU 502 and the overall computer architecture 500 from a general-purpose computing system into a special-purpose computing system customized to facilitate the functionality presented herein. The CPU 502 may be constructed from any number of transistors or other discrete circuit elements, which may individually or collectively assume any number of states. More specifically, the CPU 502 may operate as a finite-state machine, in response to executable instructions contained within the software modules disclosed herein. These computer-executable instructions may transform the CPU 502 by specifying how the CPU 502 transitions between states, thereby transforming the transistors or other discrete hardware elements constituting the CPU 502.

Encoding the software modules presented herein also may transform the physical structure of the computer-readable media presented herein. The specific transformation of physical structure may depend on various factors, in different implementations of this description. Examples of such factors may include, but are not limited to, the technology used to implement the computer-readable media, whether the computer-readable media is characterized as primary or secondary storage, and the like. For example, if the computer-readable media is implemented as semiconductor-based memory, the software disclosed herein may be encoded on the computer-readable media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer architecture 500 in order to store and execute the software components presented herein. It also should be appreciated that the computer architecture 500 may include other types of computing devices, including hand-held computers, embedded computer systems, personal digital assistants, and other types of computing devices known to those skilled in the art. It is also contemplated that the computer architecture 500 may not include all of the components shown in FIG. 5, may include other components that are not explicitly shown in FIG. 5, or may utilize an architecture completely different than that shown in FIG. 5.

Figure 6:
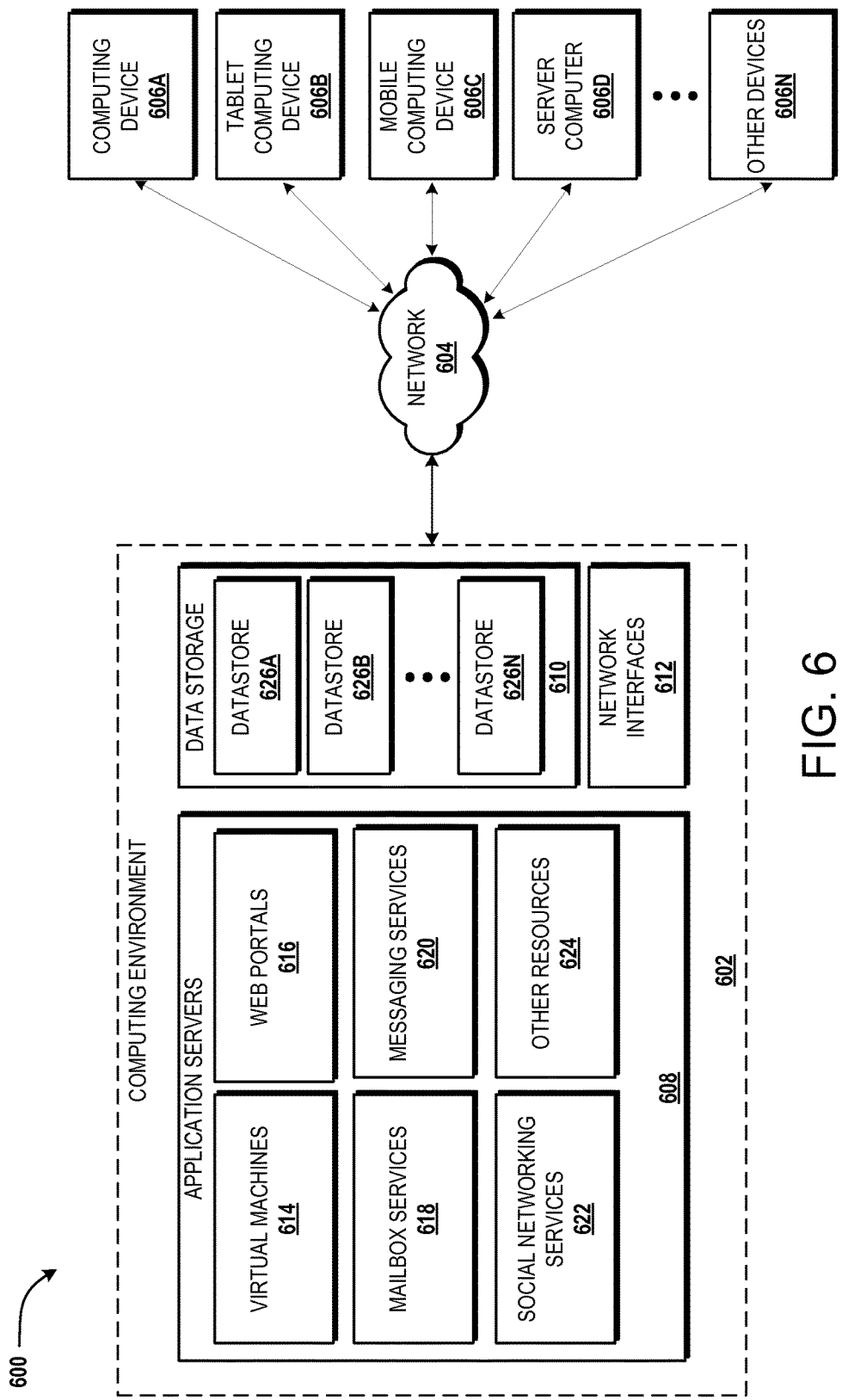
FIG. 6 is a diagram illustrating a distributed computing environment capable of implementing aspects of the techniques and technologies presented herein.

FIG. 6 depicts an illustrative distributed computing environment 600 capable of executing the software components described herein for providing enhanced motion tracking using a transportable inertial sensor, among other aspects. Thus, the distributed computing environment 600 illustrated in FIG. 6 can be utilized to execute any aspects of the software components presented herein. For example, the distributed computing environment 600 can be utilized to execute aspects of the web browser 510, the content manager 105 and/or other software components described herein.

According to various implementations, the distributed computing environment 600 includes a computing environment 602 operating on, in communication with, or as part of the network 604. The network 604 may be or may include the network 756, described above with reference to FIG. 5. The network 604 also can include various access networks. One or more client devices 606A-606N (hereinafter referred to collectively and/or generically as "clients 606") can communicate with the computing environment 602 via the network 604 and/or other connections (not illustrated in FIG. 6). In one illustrated configuration, the clients 606 include a computing device 606A such as a laptop computer, a desktop computer, or other computing device; a slate or tablet computing device ("tablet computing device") 606B; a mobile computing device 606C such as a mobile telephone, a smart phone, or other mobile computing device; a server computer 606D; and/or other devices 606N. It should be understood that any number of clients 606 can communicate with the computing environment 602. Two example computing architectures for the clients 606 are illustrated and described herein with reference to FIGS. 5 and 7. It should be understood that the illustrated clients 606 and computing architectures illustrated and described herein are illustrative, and should not be construed as being limited in any way.

In the illustrated configuration, the computing environment 602 includes application servers 608, data storage 610, and one or more network interfaces 612. According to various implementations, the functionality of the application servers 608 can be provided by one or more server computers that are executing as part of, or in communication with, the network 604. The application servers 608 can host various services, virtual machines, portals, and/or other resources. In the illustrated configuration, the application servers 608 host one or more virtual machines 614 for hosting applications or other functionality. According to various implementations, the virtual machines 614 host one or more applications and/or software modules for providing enhanced motion tracking using a transportable inertial sensor. It should be understood that this configuration is illustrative, and should not be construed as being limiting in any way. The application servers 608 also host or provide access to one or more portals, link pages, Web sites, and/or other information ("Web portals") 616.

According to various implementations, the application servers 608 also include one or more mailbox services 618 and one or more messaging services 620. The mailbox services 618 can include electronic mail ("email") services. The mailbox services 618 also can include various personal information management ("PIM") services including, but not limited to, calendar services, contact management services, collaboration services, and/or other services. The messaging services 620 can include, but are not limited to, instant messaging services, chat services, forum services, and/or other communication services.

The application servers 608 also may include one or more social networking services 622. The social networking services 622 can include various social networking services including, but not limited to, services for sharing or posting status updates, instant messages, links, photos, videos, and/or other information; services for commenting or displaying interest in articles, products, blogs, or other resources; and/or other services. In some configurations, the social networking services 622 are provided by or include the FACEBOOK social networking service, the LINKEDIN professional networking service, the MYSPACE social networking service, the FOURSQUARE geographic networking service, the YAMMER office colleague networking service, and the like. In other configurations, the social networking services 622 are provided by other services, sites, and/or providers that may or may not be explicitly known as social networking providers. For example, some web sites allow users to interact with one another via email, chat services, and/or other means during various activities and/or contexts such as reading published articles, commenting on goods or services, publishing, collaboration, gaming, and the like. Examples of such services include, but are not limited to, the WINDOWS LIVE service and the XBOX LIVE service from Microsoft Corporation in Redmond, Wash. Other services are possible and are contemplated.

The social networking services 622 also can include commenting, blogging, and/or micro blogging services. Examples of such services include, but are not limited to, the YELP commenting service, the KUDZU review service, the OFFICETALK enterprise micro blogging service, the TWITTER messaging service, the GOOGLE BUZZ service, and/or other services. It should be appreciated that the above lists of services are not exhaustive and that numerous additional and/or alternative social networking services 622 are not mentioned herein for the sake of brevity. As such, the above configurations are illustrative, and should not be construed as being limited in any way. According to various implementations, the social networking services 622 may host one or more applications and/or software modules for providing the functionality described herein for providing enhanced motion tracking using a transportable inertial sensor. For instance, any one of the application servers 608 may communicate or facilitate the functionality and features described herein. For instance, a social networking application, mail client, messaging client or a browser running on a phone or any other client 606 may communicate with a networking service 622 and facilitate the functionality, even in part, described above with respect to FIG. 4.

As shown in FIG. 6, the application servers 608 also can host other services, applications, portals, and/or other resources ("other resources") 624. The other resources 624 can include, but are not limited to, document sharing, rendering or any other functionality. It thus can be appreciated that the computing environment 602 can provide integration of the concepts and technologies disclosed herein provided herein with various mailbox, messaging, social networking, and/or other services or resources.

As mentioned above, the computing environment 602 can include the data storage 610. According to various implementations, the functionality of the data storage 610 is provided by one or more databases operating on, or in communication with, the network 604. The functionality of the data storage 610 also can be provided by one or more server computers configured to host data for the computing environment 602. The data storage 610 can include, host, or provide one or more real or virtual datastores 626A-626N (hereinafter referred to collectively and/or generically as "datastores 626"). The datastores 626 are configured to host data used or created by the application servers 608 and/or other data. Although not illustrated in FIG. 6, the datastores 626 also can host or store web page documents, word documents, presentation documents, data structures, algorithms for execution by a recommendation engine, and/or other data utilized by any application program or another module, such as the content manager 105. Aspects of the datastores 626 may be associated with a service for storing files.

The computing environment 602 can communicate with, or be accessed by, the network interfaces 612. The network interfaces 612 can include various types of network hardware and software for supporting communications between two or more computing devices including, but not limited to, the clients 606 and the application servers 608. It should be appreciated that the network interfaces 612 also may be utilized to connect to other types of networks and/or computer systems.

It should be understood that the distributed computing environment 600 described herein can provide any aspects of the software elements described herein with any number of virtual computing resources and/or other distributed computing functionality that can be configured to execute any aspects of the software components disclosed herein. According to various implementations of the concepts and technologies disclosed herein, the distributed computing environment 600 provides the software functionality described herein as a service to the clients 606. It should be understood that the clients 606 can include real or virtual machines including, but not limited to, server computers, web servers, personal computers, mobile computing devices, smart phones, and/or other devices. As such, various configurations of the concepts and technologies disclosed herein enable any device configured to access the distributed computing environment 600 to utilize the functionality described herein for providing enhanced motion tracking using a transportable inertial sensor, among other aspects. In one specific example, as summarized above, techniques described herein may be implemented, at least in part, by the web browser application 510 of FIG. 5, which works in conjunction with the application servers 608 of FIG. 6.

Figure 7:
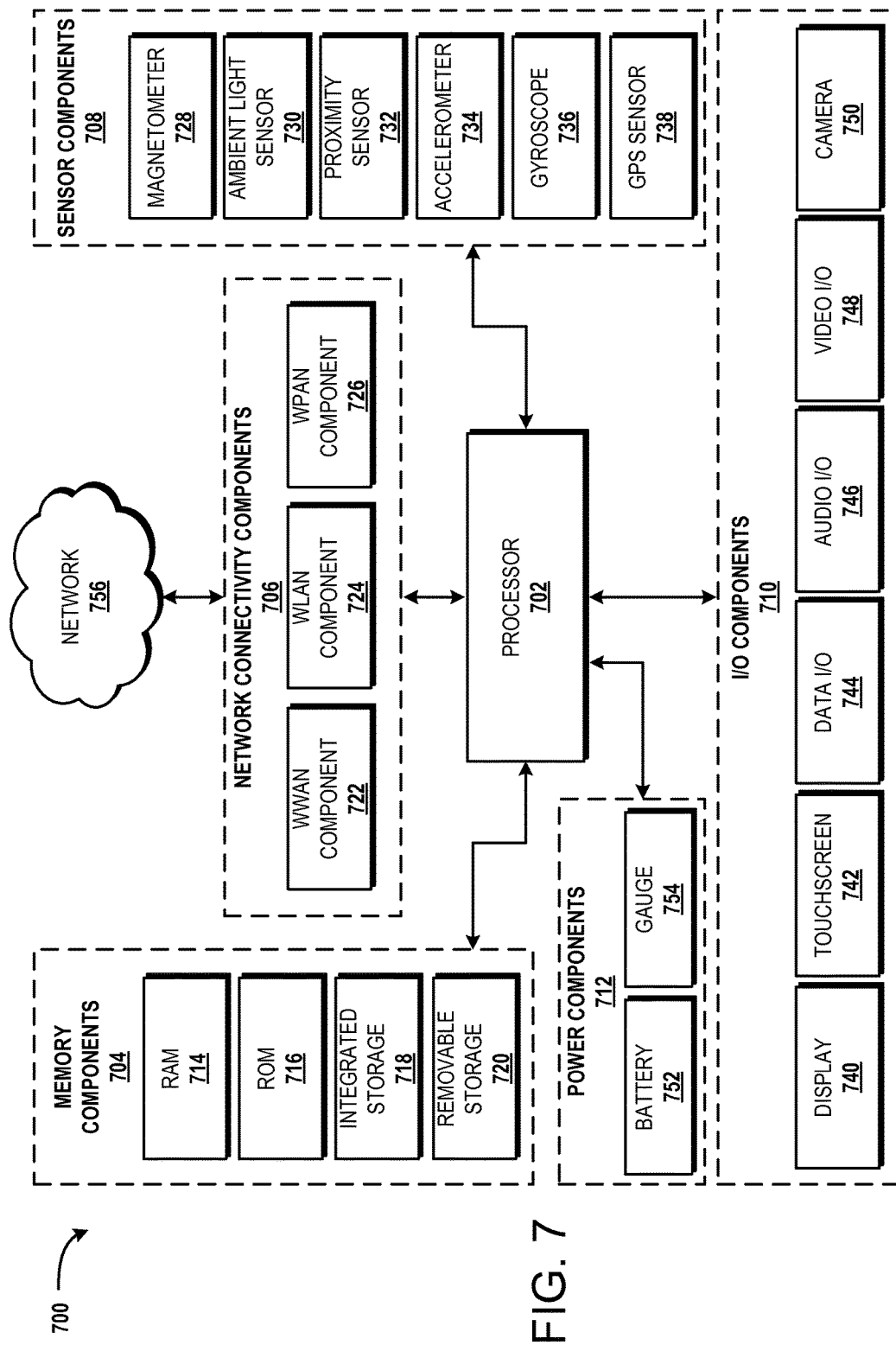
FIG. 7 is a computer architecture diagram illustrating a computing device architecture for a computing device capable of implementing aspects of the techniques and technologies presented herein.

Turning now to FIG. 7, an illustrative computing device architecture 700 for a computing device that is capable of executing various software components described herein for providing enhanced motion tracking using a transportable inertial sensor. The computing device architecture 700 is applicable to computing devices that facilitate mobile computing due, in part, to form factor, wireless connectivity, and/or battery-powered operation. In some configurations, the computing devices include, but are not limited to, mobile telephones, tablet devices, slate devices, portable video game devices, and the like. The computing device architecture 700 is applicable to any of the clients 606 shown in FIG. 6. Moreover, aspects of the computing device architecture 700 may be applicable to traditional desktop computers, portable computers (e.g., laptops, notebooks, ultra-portables, and netbooks), server computers, and other computer systems, such as described herein with reference to FIG. 5. For example, the single touch and multi-touch aspects disclosed herein below may be applied to desktop computers that utilize a touchscreen or some other touch-enabled device, such as a touch-enabled track pad or touch-enabled mouse.

The computing device architecture 700 illustrated in FIG. 7 includes a processor 702, memory components 704, network connectivity components 706, sensor components 708, input/output components 710, and power components 712. In the illustrated configuration, the processor 702 is in communication with the memory components 704, the network connectivity components 706, the sensor components 708, the input/output ("I/O") components 710, and the power components 712. Although no connections are shown between the individuals components illustrated in FIG. 7, the components can interact to carry out device functions. In some configurations, the components are arranged so as to communicate via one or more busses (not shown).

The processor 702 includes a central processing unit ("CPU") configured to process data, execute computer-executable instructions of one or more application programs, and communicate with other components of the computing device architecture 700 in order to perform various functionality described herein. The processor 702 may be utilized to execute aspects of the software components presented herein and, particularly, those that utilize, at least in part, a touch-enabled input.

In some configurations, the processor 702 includes a graphics processing unit ("GPU") configured to accelerate operations performed by the CPU, including, but not limited to, operations performed by executing general-purpose scientific and/or engineering computing applications, as well as graphics-intensive computing applications such as high resolution video (e.g., 720P, 1080P, and higher resolution), video games, three-dimensional ("3D") modeling applications, and the like. In some configurations, the processor 702 is configured to communicate with a discrete GPU (not shown). In any case, the CPU and GPU may be configured in accordance with a co-processing CPU/GPU computing model, wherein the sequential part of an application executes on the CPU and the computationally-intensive part is accelerated by the GPU.

In some configurations, the processor 702 is, or is included in, a system-on-chip ("SoC") along with one or more of the other components described herein below. For example, the SoC may include the processor 702, a GPU, one or more of the network connectivity components 706, and one or more of the sensor components 708. In some configurations, the processor 702 is fabricated, in part, utilizing a package-on-package ("PoP") integrated circuit packaging technique. The processor 702 may be a single core or multi-core processor.

The processor 702 may be created in accordance with an ARM architecture, available for license from ARM HOLDINGS of Cambridge, United Kingdom. Alternatively, the processor 702 may be created in accordance with an x86 architecture, such as is available from INTEL CORPORATION of Mountain View, Calif. and others. In some configurations, the processor 702 is a SNAPDRAGON SoC, available from QUALCOMM of San Diego, Calif., a TEGRA SoC, available from NVIDIA of Santa Clara, Calif., a HUMMINGBIRD SoC, available from SAMSUNG of Seoul, South Korea, an Open Multimedia Application Platform ("OMAP") SoC, available from TEXAS INSTRUMENTS of Dallas, Tex., a customized version of any of the above SoCs, or a proprietary SoC.

The memory components 704 include a random access memory ("RAM") 714, a read-only memory ("ROM") 716, an integrated storage memory ("integrated storage") 718, and a removable storage memory ("removable storage") 720. In some configurations, the RAM 714 or a portion thereof, the ROM 716 or a portion thereof, and/or some combination the RAM 714 and the ROM 716 is integrated in the processor 702. In some configurations, the ROM 716 is configured to store a firmware, an operating system or a portion thereof (e.g., operating system kernel), and/or a bootloader to load an operating system kernel from the integrated storage 718 and/or the removable storage 720.

The integrated storage 718 can include a solid-state memory, a hard disk, or a combination of solid-state memory and a hard disk. The integrated storage 718 may be soldered or otherwise connected to a logic board upon which the processor 702 and other components described herein also may be connected. As such, the integrated storage 718 is integrated in the computing device. The integrated storage 718 is configured to store an operating system or portions thereof, application programs, data, and other software components described herein.

The removable storage 720 can include a solid-state memory, a hard disk, or a combination of solid-state memory and a hard disk. In some configurations, the removable storage 720 is provided in lieu of the integrated storage 718. In other configurations, the removable storage 720 is provided as additional optional storage. In some configurations, the removable storage 720 is logically combined with the integrated storage 718 such that the total available storage is made available as a total combined storage capacity. In some configurations, the total combined capacity of the integrated storage 718 and the removable storage 720 is shown to a user instead of separate storage capacities for the integrated storage 718 and the removable storage 720.

The removable storage 720 is configured to be inserted into a removable storage memory slot (not shown) or other mechanism by which the removable storage 720 is inserted and secured to facilitate a connection over which the removable storage 720 can communicate with other components of the computing device, such as the processor 702. The removable storage 720 may be embodied in various memory card formats including, but not limited to, PC card, CompactFlash card, memory stick, secure digital ("SD"), miniSD, microSD, universal integrated circuit card ("UICC") (e.g., a subscriber identity module ("SIM") or universal SIM ("USIM")), a proprietary format, or the like.

It can be understood that one or more of the memory components 704 can store an operating system. According to various configurations, the operating system includes, but is not limited to WINDOWS MOBILE OS from Microsoft Corporation of Redmond, Wash., WINDOWS PHONE OS from Microsoft Corporation, WINDOWS from Microsoft Corporation, PALM WEBOS from Hewlett-Packard Company of Palo Alto, Calif., BLACKBERRY OS from Research In Motion Limited of Waterloo, Ontario, Canada, IOS from Apple Inc. of Cupertino, Calif., and ANDROID OS from Google Inc. of Mountain View, Calif. Other operating systems are contemplated.

The network connectivity components 706 include a wireless wide area network component ("WWAN component") 722, a wireless local area network component ("WLAN component") 724, and a wireless personal area network component ("WPAN component") 726. The network connectivity components 706 facilitate communications to and from the network 756 or another network, which may be a WWAN, a WLAN, or a WPAN. Although only the network 756 is illustrated, the network connectivity components 706 may facilitate simultaneous communication with multiple networks, including the network 604 of FIG. 6. For example, the network connectivity components 706 may facilitate simultaneous communications with multiple networks via one or more of a WWAN, a WLAN, or a WPAN.

The network 756 may be or may include a WWAN, such as a mobile telecommunications network utilizing one or more mobile telecommunications technologies to provide voice and/or data services to a computing device utilizing the computing device architecture 700 via the WWAN component 722. The mobile telecommunications technologies can include, but are not limited to, Global System for Mobile communications ("GSM"), Code Division Multiple Access ("CDMA") ONE, CDMA7000, Universal Mobile Telecommunications System ("UMTS"), Long Term Evolution ("LTE"), and Worldwide Interoperability for Microwave Access ("WiMAX"). Moreover, the network 756 may utilize various channel access methods (which may or may not be used by the aforementioned standards) including, but not limited to, Time Division Multiple Access ("TDMA"), Frequency Division Multiple Access ("FDMA"), CDMA, wideband CDMA ("W-CDMA"), Orthogonal Frequency Division Multiplexing ("OFDM"), Space Division Multiple Access ("SDMA"), and the like. Data communications may be provided using General Packet Radio Service ("GPRS"), Enhanced Data rates for Global Evolution ("EDGE"), the High-Speed Packet Access ("HSPA") protocol family including High-Speed Downlink Packet Access ("HSDPA"), Enhanced Uplink ("EUL") or otherwise termed High-Speed Uplink Packet Access ("HSUPA"), Evolved HSPA ("HSPA+"), LTE, and various other current and future wireless data access standards. The network 756 may be configured to provide voice and/or data communications with any combination of the above technologies. The network 756 may be configured to or adapted to provide voice and/or data communications in accordance with future generation technologies.

In some configurations, the WWAN component 722 is configured to provide dual-multi-mode connectivity to the network 756. For example, the WWAN component 722 may be configured to provide connectivity to the network 756, wherein the network 756 provides service via GSM and UMTS technologies, or via some other combination of technologies. Alternatively, multiple WWAN components 722 may be utilized to perform such functionality, and/or provide additional functionality to support other non-compatible technologies (i.e., incapable of being supported by a single WWAN component). The WWAN component 722 may facilitate similar connectivity to multiple networks (e.g., a UMTS network and an LTE network).

The network 756 may be a WLAN operating in accordance with one or more Institute of Electrical and Electronic Engineers ("IEEE") 802.11 standards, such as IEEE 802.11a, 802.11b, 802.11g, 802.11n, and/or future 802.11 standard (referred to herein collectively as WI-FI). Draft 802.11 standards are also contemplated. In some configurations, the WLAN is implemented utilizing one or more wireless WI-FI access points. In some configurations, one or more of the wireless WI-FI access points are another computing device with connectivity to a WWAN that are functioning as a WI-FI hotspot. The WLAN component 724 is configured to connect to the network 756 via the WI-FI access points. Such connections may be secured via various encryption technologies including, but not limited, WI-FI Protected Access ("WPA"), WPA2, Wired Equivalent Privacy ("WEP"), and the like.

The network 756 may be a WPAN operating in accordance with Infrared Data Association ("IrDA"), BLUETOOTH, wireless Universal Serial Bus ("USB"), Z-Wave, ZIGBEE, or some other short-range wireless technology. In some configurations, the WPAN component 726 is configured to facilitate communications with other devices, such as peripherals, computers, or other computing devices via the WPAN.

The sensor components 708 include a magnetometer 728, an ambient light sensor 730, a proximity sensor 732, an accelerometer 734, a gyroscope 736, and a Global Positioning System sensor ("GPS sensor") 738. It is contemplated that other sensors, such as, but not limited to, temperature sensors or shock detection sensors, also may be incorporated in the computing device architecture 700.

The magnetometer 728 is configured to measure the strength and direction of a magnetic field. In some configurations the magnetometer 728 provides measurements to a compass application program stored within one of the memory components 704 in order to provide a user with accurate directions in a frame of reference including the cardinal directions, north, south, east, and west. Similar measurements may be provided to a navigation application program that includes a compass component. Other uses of measurements obtained by the magnetometer 728 are contemplated.

The ambient light sensor 730 is configured to measure ambient light. In some configurations, the ambient light sensor 730 provides measurements to an application program stored within one the memory components 704 in order to automatically adjust the brightness of a display (described below) to compensate for low-light and high-light environments. Other uses of measurements obtained by the ambient light sensor 730 are contemplated.

The proximity sensor 732 is configured to detect the presence of an object or thing in proximity to the computing device without direct contact. In some configurations, the proximity sensor 732 detects the presence of a user's body (e.g., the user's face) and provides this information to an application program stored within one of the memory components 704 that utilizes the proximity information to enable or disable some functionality of the computing device. For example, a telephone application program may automatically disable a touchscreen (described below) in response to receiving the proximity information so that the user's face does not inadvertently end a call or enable/disable other functionality within the telephone application program during the call. Other uses of proximity as detected by the proximity sensor 732 are contemplated.

The accelerometer 734 is configured to measure proper acceleration. In some configurations, output from the accelerometer 734 is used by an application program as an input mechanism to control some functionality of the application program. For example, the application program may be a video game in which a character, a portion thereof, or an object is moved or otherwise manipulated in response to input received via the accelerometer 734. In some configurations, output from the accelerometer 734 is provided to an application program for use in switching between landscape and portrait modes, calculating coordinate acceleration, or detecting a fall. Other uses of the accelerometer 734 are contemplated.

The gyroscope 736 is configured to measure and maintain orientation. In some configurations, output from the gyroscope 736 is used by an application program as an input mechanism to control some functionality of the application program. For example, the gyroscope 736 can be used for accurate recognition of movement within a 3D environment of a video game application or some other application. In some configurations, an application program utilizes output from the gyroscope 736 and the accelerometer 734 to enhance control of some functionality of the application program. Other uses of the gyroscope 736 are contemplated.

The GPS sensor 738 is configured to receive signals from GPS satellites for use in calculating a location. The location calculated by the GPS sensor 738 may be used by any application program that requires or benefits from location information. For example, the location calculated by the GPS sensor 738 may be used with a navigation application program to provide directions from the location to a destination or directions from the destination to the location. Moreover, the GPS sensor 738 may be used to provide location information to an external location-based service, such as E911 service. The GPS sensor 738 may obtain location information generated via WI-FI, WIMAX, and/or cellular triangulation techniques utilizing one or more of the network connectivity components 706 to aid the GPS sensor 738 in obtaining a location fix. The GPS sensor 738 may also be used in Assisted GPS ("A-GPS") systems.

The I/O components 710 include a display 740, a touchscreen 742, a data I/O interface component ("data I/O") 744, an audio I/O interface component ("audio I/O") 746, a video I/O interface component ("video I/O") 748, and a camera 750. In some configurations, the display 740 and the touchscreen 742 are combined. In some configurations two or more of the data I/O component 744, the audio I/O component 746, and the video I/O component 748 are combined. The I/O components 710 may include discrete processors configured to support the various interface described below, or may include processing functionality built-in to the processor 702.

The display 740 is an output device configured to present information in a visual form. In particular, the display 740 may present graphical user interface ("GUI") elements, text, images, video, notifications, virtual buttons, virtual keyboards, messaging data, Internet content, device status, time, date, calendar data, preferences, map information, location information, and any other information that is capable of being presented in a visual form. In some configurations, the display 740 is a liquid crystal display ("LCD") utilizing any active or passive matrix technology and any backlighting technology (if used). In some configurations, the display 740 is an organic light emitting diode ("OLED") display. Other display types are contemplated.

The touchscreen 742, also referred to herein as a "touch-enabled screen," is an input device configured to detect the presence and location of a touch. The touchscreen 742 may be a resistive touchscreen, a capacitive touchscreen, a surface acoustic wave touchscreen, an infrared touchscreen, an optical imaging touchscreen, a dispersive signal touchscreen, an acoustic pulse recognition touchscreen, or may utilize any other touchscreen technology. In some configurations, the touchscreen 742 is incorporated on top of the display 740 as a transparent layer to enable a user to use one or more touches to interact with objects or other information presented on the display 740. In other configurations, the touchscreen 742 is a touch pad incorporated on a surface of the computing device that does not include the display 740. For example, the computing device may have a touchscreen incorporated on top of the display 740 and a touch pad on a surface opposite the display 740.

In some configurations, the touchscreen 742 is a single-touch touchscreen. In other configurations, the touchscreen 742 is a multi-touch touchscreen. In some configurations, the touchscreen 742 is configured to detect discrete touches, single touch gestures, and/or multi-touch gestures. These are collectively referred to herein as gestures for convenience. Several gestures will now be described. It should be understood that these gestures are illustrative and are not intended to limit the scope of the appended claims. Moreover, the described gestures, additional gestures, and/or alternative gestures may be implemented in software for use with the touchscreen 742. As such, a developer may create gestures that are specific to a particular application program.

In some configurations, the touchscreen 742 supports a tap gesture in which a user taps the touchscreen 742 once on an item presented on the display 740. The tap gesture may be used for various reasons including, but not limited to, opening or launching whatever the user taps. In some configurations, the touchscreen 742 supports a double tap gesture in which a user taps the touchscreen 742 twice on an item presented on the display 740. The double tap gesture may be used for various reasons including, but not limited to, zooming in or zooming out in stages. In some configurations, the touchscreen 742 supports a tap and hold gesture in which a user taps the touchscreen 742 and maintains contact for at least a pre-defined time. The tap and hold gesture may be used for various reasons including, but not limited to, opening a context-specific menu.

In some configurations, the touchscreen 742 supports a pan gesture in which a user places a finger on the touchscreen 742 and maintains contact with the touchscreen 742 while moving the finger on the touchscreen 742. The pan gesture may be used for various reasons including, but not limited to, moving through screens, images, or menus at a controlled rate. Multiple finger pan gestures are also contemplated. In some configurations, the touchscreen 742 supports a flick gesture in which a user swipes a finger in the direction the user wants the screen to move. The flick gesture may be used for various reasons including, but not limited to, scrolling horizontally or vertically through menus or pages. In some configurations, the touchscreen 742 supports a pinch and stretch gesture in which a user makes a pinching motion with two fingers (e.g., thumb and forefinger) on the touchscreen 742 or moves the two fingers apart. The pinch and stretch gesture may be used for various reasons including, but not limited to, zooming gradually in or out of a website, map, or picture.

Although the above gestures have been described with reference to the use one or more fingers for performing the gestures, other appendages such as toes or objects such as styluses may be used to interact with the touchscreen 742. As such, the above gestures should be understood as being illustrative and should not be construed as being limiting in any way.

The data I/O interface component 744 is configured to facilitate input of data to the computing device and output of data from the computing device. In some configurations, the data I/O interface component 744 includes a connector configured to provide wired connectivity between the computing device and a computer system, for example, for synchronization operation purposes. The connector may be a proprietary connector or a standardized connector such as USB, micro-USB, mini-USB, or the like. In some configurations, the connector is a dock connector for docking the computing device with another device such as a docking station, audio device (e.g., a digital music player), or video device.

The audio I/O interface component 746 is configured to provide audio input and/or output capabilities to the computing device. In some configurations, the audio I/O interface component 746 includes a microphone configured to collect audio signals. In some configurations, the audio I/O interface component 746 includes a headphone jack configured to provide connectivity for headphones or other external speakers. In some configurations, the audio I/O interface component 746 includes a speaker for the output of audio signals. In some configurations, the audio I/O interface component 746 includes an optical audio cable out.

The video I/O interface component 748 is configured to provide video input and/or output capabilities to the computing device. In some configurations, the video I/O interface component 748 includes a video connector configured to receive video as input from another device (e.g., a video media player such as a DVD or BLURAY player) or send video as output to another device (e.g., a monitor, a television, or some other external display). In some configurations, the video I/O interface component 748 includes a High-Definition Multimedia Interface ("HDMI"), mini-HDMI, micro-HDMI, DisplayPort, or proprietary connector to input/output video content. In some configurations, the video I/O interface component 748 or portions thereof is combined with the audio I/O interface component 746 or portions thereof.

The camera 750 can be configured to capture still images and/or video. The camera 750 may utilize a charge coupled device ("CCD") or a complementary metal oxide semiconductor ("CMOS") image sensor to capture images. In some configurations, the camera 750 includes a flash to aid in taking pictures in low-light environments. Settings for the camera 750 may be implemented as hardware or software buttons.

Although not illustrated, one or more hardware buttons may also be included in the computing device architecture 700. The hardware buttons may be used for controlling some operational aspect of the computing device. The hardware buttons may be dedicated buttons or multi-use buttons. The hardware buttons may be mechanical or sensor-based.

The illustrated power components 712 include one or more batteries 752, which can be connected to a battery gauge 754. The batteries 752 may be rechargeable or disposable. Rechargeable battery types include, but are not limited to, lithium polymer, lithium ion, nickel cadmium, and nickel metal hydride. Each of the batteries 752 may be made of one or more cells.

The battery gauge 754 can be configured to measure battery parameters such as current, voltage, and temperature. In some configurations, the battery gauge 754 is configured to measure the effect of a battery's discharge rate, temperature, age and other factors to predict remaining life within a certain percentage of error. In some configurations, the battery gauge 754 provides measurements to an application program that is configured to utilize the measurements to present useful power management data to a user. Power management data may include one or more of a percentage of battery used, a percentage of battery remaining, a battery condition, a remaining time, a remaining capacity (e.g., in watt hours), a current draw, and a voltage.

The power components 712 may also include a power connector, which may be combined with one or more of the aforementioned I/O components 710. The power components 712 may interface with an external power system or charging equipment via an I/O component.

The disclosure presented herein may be considered in view of the following clauses.

Clause 1: An apparatus for tracking the motion of an object, comprising: a first inertial sensor mounted on a portable device; a second inertial sensor mounted to the object; and a component configured to receive a signal from the first inertial sensor to determine a frame of reference, to receive a signal from the second inertial sensor to determine movement of the object within the frame of reference, and to determine that the frame of reference is established.

Clause 2: The apparatus of clause 1, wherein the component is configured to detect movement of the object within the frame of reference when the frame of reference is established.

Clause 3: The apparatus of clauses 1-2, wherein determining that the frame of reference is established is based, at least in part, on the signal from the first inertial sensor.

Clause 4: The apparatus of clauses 1-3, wherein determining that the frame of reference is established is based, at least in part, on the signal from the second inertial sensor.

Clause 5: The apparatus of clauses 1-4, wherein determining that the frame of reference is established is based, at least in part, on the signal from the first inertial sensor and the signal from the second inertial sensor.

Clause 6: The apparatus of clauses 1-5, wherein determining that the frame of reference is established is based, at least in part, on the signal from the first inertial sensor and contextual data received by the component.

Clause 7: The apparatus of clauses 1-6, wherein the contextual data identifies a location of the portable device, and wherein determining that the frame of reference is established is based, at least in part, on the location of the portable device.

Clause 8: The apparatus of clauses 1-7, wherein the component comprises: a processor; and a computer-readable storage medium in communication with the processor, the computer-readable storage medium having computer-executable instructions stored thereupon which, when executed by the processor, cause the component to interpret a pattern of the signal from the first inertial sensor, and determine that the frame of reference is established based on the pattern.

Clause 9: The apparatus of clauses 1-8, wherein the component comprises: a processor; and a computer-readable storage medium in communication with the processor, the computer-readable storage medium having computer-executable instructions stored thereupon which, when executed by the processor, cause the component to obtain data identifying a threshold, monitor the signal from the first inertial sensor to determine if the signal from the first inertial sensor meets the threshold, and determine that the frame of reference is established if the signal from the first inertial sensor meets the threshold.

Clause 10: An example including: receiving a signal from a first inertial sensor mounted on an object; receiving a signal from a second inertial sensor mounted on a portable device; determining if a frame of reference is established, wherein the frame of reference is based, at least in part, on the signal from the second inertial sensor; and if it is determined that the frame of reference is established, processing the signal from the first inertial sensor and the signal from the second inertial sensor to detect movement of the object within the frame of reference.

Clause 11: The example of clause 10, wherein determining if the frame of reference is established is based, at least in part, on the signal from the first inertial sensor.

Clause 12: The computer of clauses 10-11, wherein determining if the frame of reference is established is based, at least in part, on the signal from the second inertial sensor.

Clause 13: The computer of clauses 10-12, further comprising: if it is determined that the frame of reference is established, causing a generation of a signal to provide a notification; receiving an input in response to the notification; if the input indicates an acceptance, processing the signal from the first inertial sensor and the signal from the second inertial sensor to detect movement of the object within the frame of reference; and if the input indicates a rejection, processing the signal from the first inertial sensor to detect movement of the object.

Clause 14: The computer of clauses 10-13, wherein determining if the frame of reference is established is based, at least in part, on the signal from the second inertial sensor and contextual data.

Clause 15: The computer of clauses 10-14, wherein the contextual data identifies a location of the portable device, and wherein determining if the frame of reference is established is based, at least in part, on the location of the portable device.

Clause 16: The computer of clauses 10-15, wherein the contextual data defines user activity, and wherein determining if the frame of reference is established is based, at least in part, on the user activity.

Clause 17: A computer-readable storage medium having computer-executable instructions stored thereupon which, when executed by a computer, cause the computer to: receive a signal from a first inertial sensor mounted to a first device; receive a signal from a second inertial sensor mounted on a second device; determine if a frame of reference is established, wherein the frame of reference is based, at least in part, on the signal from the second inertial sensor; and if it is determined that the frame of reference is established, processing the signal from the first inertial sensor and the signal from the second inertial sensor to detect movement of the first device within the frame of reference.

Clause 18: The computer-readable storage medium of clause 17, wherein determining that the frame of reference is established is based, at least in part, on the signal from the first inertial sensor.

Clause 19: The computer-readable storage medium of clauses 17 and 18, wherein determining that the frame of reference is established is based, at least in part, on the signal from the second inertial sensor.

Clause 20: The computer-readable storage medium of clauses 17-19, wherein determining that the frame of reference is established is based, at least in part, on the signal from the first inertial sensor and the signal from the second inertial sensor.

Based on the foregoing, it should be appreciated that concepts and technologies have been disclosed herein that provide enhanced motion tracking using a transportable inertial sensor. Although the subject matter presented herein has been described in language specific to computer structural features, methodological and transformative acts, specific computing machinery, and computer readable media, it is to be understood that the invention defined in the appended claims is not necessarily limited to the specific features, acts, or media described herein. Rather, the specific features, acts and mediums are disclosed as example forms of implementing the claims.

The subject matter described above is provided by way of illustration only and should not be construed as limiting. Various modifications and changes may be made to the subject matter described herein without following the example configurations and applications illustrated and described, and without departing from the true spirit and scope of the present invention, which is set forth in the following claims.

What is claimed is:

1. An apparatus comprising:
   a first inertial sensor mounted on a portable device of a user;
   a second inertial sensor mounted on a tracking device of the user being carried by a moving platform; and
   a computer-readable storage medium storing executable instructions configured to:
     receive, from the portable device, input that indicates the portable device is affixed or secured to the moving platform,
     receive, from the first inertial sensor, a signal useable to determine an established frame of reference based at least in part on the portable device being affixed or secured to the moving platform,
     receive, from the second inertial sensor, a signal useable to determine movement of the tracking device within the established frame of reference;
     provide a notification,
     receive a response to the notification, and
     based on the response indicating an acceptance, process the signal received from the second inertial sensor and the signal received from the first inertial sensor to determine the movement of the tracking device within the established frame of reference.

2. The apparatus of claim 1, wherein the executable instructions are further configured to track the movement of the tracking device within the established frame of reference.

3. The apparatus of claim 1, wherein the executable instructions are further configured to determine that the established frame of reference has been established based, at least in part, on the signal received from the first inertial sensor.

4. The apparatus of claim 1, wherein the executable instructions are further configured to determine that the established frame of reference has been established based, at least in part, on the signal received from the second inertial sensor.

5. The apparatus of claim 1, wherein the executable instructions are further configured to determine that the established frame of reference has been established based, at least in part, on the signal received from the first inertial sensor and the signal received from the second inertial sensor.

6. The apparatus of claim 1, wherein the executable instructions are further configured to determine that the established frame of reference has been established based, at least in part, on the signal received from the first inertial sensor and contextual data received by the tracking device.

7. The apparatus of claim 6, wherein the contextual data identifies a location of the portable device.

8. The apparatus of claim 1, wherein the tracking device comprises a processor in communication with the computer-readable storage medium, the executable instructions further configured to cause the tracking device to:
    interpret a pattern of the signal received from the first inertial sensor, and
    determine that the established frame of reference has been established based, at least in part, on the pattern.

9. The apparatus of claim 1, wherein the tracking device comprises a processor in communication with the computer-readable storage medium, the executable instructions further configured to cause the tracking device to:
    obtain data identifying a threshold,
    monitor the signal received from the first inertial sensor to determine that the signal received from the first inertial sensor meets the threshold, and
    determine that the established frame of reference has been established based, at least in part, the signal received from the first inertial sensor meeting the threshold.

10. A computer-implemented method, comprising:
    receiving, from a portable device of a user, input that indicates the portable device is affixed or secured to a moving platform,
    receiving a signal from a first inertial sensor mounted on the portable device;
    receiving a signal from a second inertial sensor mounted on a tracking device of the user being carried by the moving platform;
    determining, based at least in part on the portable device being affixed or secured to the moving platform and the signal received from the first inertial sensor, that a frame of reference is established;
    providing a notification;
    receiving a response to the notification; and
    based on the response indicating an acceptance, processing the signal received from the second inertial sensor and the signal received from the first inertial sensor to detect movement of the tracking device within the frame of reference.

11. The computer-implemented method of claim 10, wherein determining that the frame of reference is established is further based, at least in part, on the signal received from the second inertial sensor.

12. The computer-implemented method of claim 10, wherein determining that the frame of reference is established is further based, at least in part, on contextual data.

13. The computer-implemented method of claim 12, wherein the contextual data identifies a location of the portable device.

14. The computer-implemented method of claim 12, wherein the contextual data defines user activity.

15. A device of a user comprising:
    a processor; and
    a computer-readable storage medium storing instructions that, when executed by the processor, cause the device to:
        receive, from a portable device of the user, input that indicates the portable device is affixed or secured to a moving platform,
        receive a signal from a first inertial sensor mounted on the portable device;
        receive a signal from a second inertial sensor being carried by the moving platform, the second inertial sensor associated with the device;
        determine, based at least in part on the portable device being affixed or secured to the moving platform and the signal received from the first inertial sensor, that a frame of reference is established;
        provide a notification;
        receive a response to the notification; and
        based on the response indicating an acceptance, process the signal received from the second inertial sensor and the signal received from the first inertial sensor to detect movement of the device within the frame of reference.

16. The device of claim 15, wherein determining that the frame of reference is established is further based, at least in part, on contextual data.

17. The device of claim 16, wherein the contextual data identifies a location of the portable device.

18. The device of claim 16, wherein the contextual data defines user activity.

* * * * *